United States Patent
Holmquist et al.

(10) Patent No.: US 7,462,690 B2
(45) Date of Patent: Dec. 9, 2008

(54) PEPTIDE AMIDATION PROCESS

(75) Inventors: Barton Holmquist, Eagle, NE (US); Daniel Strydom, Lincoln, NE (US)

(73) Assignee: Restoragen, Inc., Lincoln, NE (US)

( * ) Notice: Subject to any disclaimer, the term of this patent is extended or adjusted under 35 U.S.C. 154(b) by 339 days.

(21) Appl. No.: 10/997,081

(22) Filed: Nov. 24, 2004

(65) Prior Publication Data

US 2005/0287632 A1 Dec. 29, 2005

Related U.S. Application Data

(63) Continuation of application No. PCT/US03/16648, filed on May 23, 2003.

(60) Provisional application No. 60/383,362, filed on May 24, 2002.

(51) Int. Cl.
*C07K 1/107* (2006.01)

(52) U.S. Cl. .................................................. 530/345

(58) Field of Classification Search ....................... None
See application file for complete search history.

(56) References Cited

U.S. PATENT DOCUMENTS

| 5,352,771 | A | 10/1994 | Kostic et al. |
| 5,393,924 | A | 2/1995 | Tafesh et al. |
| 5,457,066 | A | 10/1995 | Frank et al. |
| 6,660,758 | B1 | 12/2003 | Nicolaou et al. |
| 6,660,763 | B2 | 12/2003 | Tang et al. |
| 2005/0227313 | A1 | 10/2005 | Seo et al. |

OTHER PUBLICATIONS

T.N. Parac and N.M. Kostić. J. Am. Chem. Soc. (1996) 118(1), pp. 51-58.*
L. Zhu et al. J. Am. Chem. Soc. (1994) 116(12), pp. 5218-5224.*
S.-H. Park et al. Biochem. J. (2002) 388, pp. 171-182.*
Drexler, C., et al., "Palladium(II) and Platinum(II) Complexes with 1,5-Dithiacyclooctane (dtco): Structures of [PD(dtco)CI2] and [Pd(dcto)2](NO3)2 and Kenetics of Ligand Substitution in [Pd(dcto)2]2+ by Bidentate Ligands", *Inorg. Chem.*, 30, (1991), 1297-1302.
Holhann, et al., "Site and Equilibrium Data for Substitution Reactions of Aqua(etheylenedlamine)palladium(II) with Chloride in Aqueous Solution.", *Inorganic Chemica Acta*, 174, (1990),87-92.
"International Application No. PCT/US03/16648 International Preliminary Examination Report mailed Dec. 13, 2004", 4 pgs.
"International Application No. PCT/US03/16648 International Search Report mailed May, 27, 2004", 6 pgs.
"International Application No. PCT/US03/16648 International Written Opinion mailed Sep. 7, 2004", 6 pgs.
"International Application No. PCT/US2003/016647 International Preliminary Examination Report mailed Sep. 7, 2004", 8 pgs.
"International Application No. PCT/US2003/016647 International Search Report mailed Jul. 2, 2004", 4 pgs.
"International Preliminary Examination Report dated Jan. 28, 2005 in Serial No. PCT/US03/16468", 4 pgs.

"International Search Report dated Jan. 15, 2004 in Serial No. PCT/US2003/016468", 3 pgs.
"International Written Opinion dated Oct. 7, 2004 in Serial No. PCT/US03/16468", 3 pgs.
Djuran, M. I., et al., "Hydrolysis of amide bond in histidine-containing peptides promoted by chelated amino acid palladium(II) complexes: dependence of hydrolytic pathway on the coordination modes of the peptides", *Polyhedron*, 18(27), (Sep. 14, 1999), 3611-3616.
Dou, F., et al., "Preliminary study on the cleavage of fusion protein GST-CMIV with palladium(II) complex.", *Prep. Biochem & Biotechnol.*, 30(1), (Feb. 2000),69-78.
Drexler, C, et al., "Palladium (II) and platinum (II) complexes with 1,5-dithiacyclooctane(dtco-structures of Pd(dtco)CI2 and Pd(dtco2)(NO3)2 and kinetics of ligand substitution in [Pd(dtco2)]2plus by bidenate ligands", *Inorganic Chemistry*, 30c, (1991), 1297-1302.
F.Dou, et al., "Preliminary study on the cleavage of chimeric protein GST-CMIV with palladate(II) complex", *Prep Biochem and Biotechnol*, 301(1), (2000),69-78.
Hohmann, H, et al., "Rate and equilibrium data for substitution reactions of diaqua(ethylenediamine)palladium(II) with chloride in aqueous solution", *Inorg. Chim. Acta*, 174(1), (1990),87-92.
Milovic, N. M., et al., "Palladium(II) and platinum(II) complexes as synthetic peptidases", *Met Ions Biol Syst.*, 38, (2001),145-186.
Milovic, N. M., et al., "Palladium(II) Complexes, as Synthetic Peptidases, Regioselectively Cleave the Second Peptide Bond "Upstream"from Methionine and Histidine Side Chains", *Journal of the American Chemical Society*, 124(17), (May 1, 2002),4759-4769.
Rau, T, et al., "Complex Formation and Ligand Substitution Reactions of (2-Picolylamine)palladium(II) with Various Biologically Relevant Ligands. Characterization of (2-Picolylamine)(1,1-cyclobutanedicarboxylato)pallidum(II)", *Inorganic Chemistry*, 36, (1997),1454-1463.
Zhu, L., et al., "Site-Specfic hudrolytic cleavage of cytochrome c and of its heme undecapeptide, promoted by coordination complexes of palladium (II)", *Journal of the American Chemical Society*, 116(12), (1994),5218-5224.
Parac, T. N., et al., "New Regioselectivity in the Cleavage of Histidine-Containing Peptides by Palladium(II) Complexes Studied by Kinetic Experiments and Molecular Dynamics Simulations", *J. Am. Chem. Soc.* 121, (1999), 3127-3135.

* cited by examiner

*Primary Examiner*—Andrew D Kosar
(74) *Attorney, Agent, or Firm*—Campbell Nelson Whipps LLC

(57) ABSTRACT

The invention provides a process for amidating a desired peptide comprising cleaving a substrate polypeptide at a $X_1$-cysteine sequence, wherein X1 is the amino acid at the peptide carboxyl-terminus and cysteine is the first amino acid of a palladium cleavage site comprising the sequence cysteine-X2-X3, wherein X2 is any amino acid, X3 is an amino acid selected from the group consisting of cysteine, histidine, or methionine, and wherein the carboxylterminus of the peptide is amidated upon cleavage at the X1-cysteine sequence.

31 Claims, 4 Drawing Sheets

```
    |<-------------------Signal sequence------------------->|<----------
            51              60              69              78              87
    ATG GCT AGC ATG ACT GGT GGA CAG CAA ATG GGT CGC GGA TCC GGC CAG GGA
     M   A   S   M   T   G   G   Q   Q   M   G   R   G   S   G   Q   G ------------------------Vg gene sequence------------------------
       96             105             114             123             132             141
    CAG GCT CAA TAT CTA GCG GCC TCC TTG GTT GTG TTC ACC AAC TAC TCG GGC
     Q   A   Q   Y   L   A   A   S   L   V   V   F   T   N   Y   S   G ------------------------->|<-------------Linker sequence-----------
          150             159             168             177             186             195
    GAC ACG GCC AGC CAG GTG GAC GTT AAC GGT CCG CGT GCT ATG GTC GAC GAC
     D   T   A   S   Q   V   D   V   N   G   P   R   A   M   V   D   D ------------------>|<-------------------------------------------------
          204             213             222             231             240
    GAC GAC AAA TGC CAC TAC GCT GAC GCT ATC TTC ACC AAC TCT TAC CGT AAA
     D   D   K   C   H   Y   A   D   A   I   F   T   N   S   Y   R   K ------------------------GRF(1-44)CACLE sequence------------------
          249             258             267             276             285             294
    GTT CTG GGT CAG CTG TCT GCT CGT AAA CTG CTG CAG GAC ATC ATG TCC CGT
     V   L   G   Q   L   S   A   R   K   L   L   Q   D   I   M   S   R -------  ---------------------------------------------------------->|
          303             312             321             330             339             345
    CAG CAG GGT GAA TCT AAC CAG GAA CGT GGT GCT CGT GCT CGT CTG TGC CGT
     Q   Q   G   E   S   N   Q   E   R   G   A   R   A   R   L   C   A

354
    TGC CAC TAA CTC TAA CTC GAG -- 3'
     C   L   E   **  L   E
```

Fig. 1

SEQUENCE LISTING

```
<160> NUMBER OF SEQ ID NOS: 43

<210> SEQ ID NO 1
<211> LENGTH: 4
<212> TYPE: PRT
<213> ORGANISM: Artificial Sequence
<220> FEATURE:
<223> OTHER INFORMATION: A synthetic substrate

<400> SEQUENCE: 1

Phe Ala Arg Ala
 1

<210> SEQ ID NO 2
<211> LENGTH: 4
<212> TYPE: PRT
<213> ORGANISM: Artificial Sequence
<220> FEATURE:
<223> OTHER INFORMATION: A synthetic substrate

<400> SEQUENCE: 2

Phe Ala Leu Ala
 1

<210> SEQ ID NO 3
<211> LENGTH: 31
<212> TYPE: PRT
<213> ORGANISM: Artificial Sequence
<220> FEATURE:
<223> OTHER INFORMATION: A synthetic chimeric protein
<220> FEATURE:
<221> NAME/KEY: SITE
<222> LOCATION: 31
<223> OTHER INFORMATION: Xaa = any amino acid
```

```
<400> SEQUENCE: 3

Met Val Asp Asp Asp Asn Gly Lys Leu Ser Gln Glu Leu His Lys
1               5                   10                  15

Leu Gln Thr Tyr Pro Arg Thr Asp Val Gly Ala Gly Thr Pro Xaa
            20                  25                  30

<210> SEQ ID NO 4
<211> LENGTH: 23
<212> TYPE: PRT
<213> ORGANISM: Artificial Sequence
<220> FEATURE:
<223> OTHER INFORMATION: ECF2: a synthetic polypeptide fragment

<400> SEQUENCE: 4

Gly Lys Leu Ser Gln Glu Leu His Lys Leu Gln Thr Tyr Pro Arg Thr
1               5                   10                  15

Asp Val Gly Ala Gly Thr Pro
            20

<210> SEQ ID NO 5
<211> LENGTH: 30
<212> TYPE: PRT
<213> ORGANISM: Artificial Sequence
<220> FEATURE:
<223> OTHER INFORMATION: A synthetic polypeptide fragment
<220> FEATURE:
<221> NAME/KEY: SITE
<222> LOCATION: 30
<223> OTHER INFORMATION: Ser is a homoserine (Hse)

<400> SEQUENCE: 5

Val Asp Asp Asp Asn Gly Lys Leu Ser Gln Glu Leu His Lys Leu
1               5                   10                  15

Gln Thr Tyr Pro Arg Thr Asp Val Gly Ala Gly Thr Pro Ser
            20                  25                  30

<210> SEQ ID NO 6
<211> LENGTH: 6
<212> TYPE: PRT
<213> ORGANISM: Artificial Sequence
<220> FEATURE:
<223> OTHER INFORMATION: A synthetic peptide

<400> SEQUENCE: 6

Val Asp Asp Asp Asn
1               5

<210> SEQ ID NO 7
<211> LENGTH: 5
<212> TYPE: PRT
<213> ORGANISM: Artificial Sequence
<220> FEATURE:
<223> OTHER INFORMATION: A synthetic peptide

<400> SEQUENCE: 7

Asp Asp Asp Asp Lys
1               5

<210> SEQ ID NO 8
<211> LENGTH: 6
<212> TYPE: PRT
<213> ORGANISM: Artificial Sequence
<220> FEATURE:
<223> OTHER INFORMATION: A synthetic peptide

<400> SEQUENCE: 8
```

Gly Gly Gly Gly Pro Arg
1               5

<210> SEQ ID NO 9
<211> LENGTH: 327
<212> TYPE: DNA
<213> ORGANISM: Artificial Sequence
<220> FEATURE:
<223> OTHER INFORMATION: A synthetic DNA sequence of the GRF chimeric
      protein

<400> SEQUENCE: 9
atggctagca tgactggtgg acagcaaatg ggtcgcggat ccggccaggg acaggctcaa      60
tatctagcgg cctccttggt tgtgttcacc aactactcgg cgacacggc cagccaggtg      120 gacgttaacg gtccgcgtgc tatggtcgac gacgacgaca aatgccacta cgctgacgct      180
atcttcacca actcttaccg taaagttctg ggtcagctgt ctgctcgtaa actgctgcag      240
gacatcatgt cccgtcagca gggtgaatct aaccaggaac gtggtgctcg tgctcgtctg      300
tgccgttgcc actaactcta actcgag                                          327

<210> SEQ ID NO 10
<211> LENGTH: 105
<212> TYPE: PRT
<213> ORGANISM: Artificial Sequence
<220> FEATURE:
<223> OTHER INFORMATION: A synthetic peptide sequence of the GRF
      chimeric protein

<400> SEQUENCE: 10

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Gly Pro Arg Ala Met
        35                  40                  45

Val Asp Asp Asp Lys Cys His Tyr Ala Asp Ala Ile Phe Thr Asn
    50                  55                  60

Ser Tyr Arg Lys Val Leu Gly Gln Leu Ser Ala Arg Lys Leu Leu Gln
65                  70                  75                  80

Asp Ile Met Ser Arg Gln Gln Gly Glu Ser Asn Gln Glu Arg Gly Ala
                85                  90                  95

Arg Ala Arg Leu Cys Ala Cys Leu Glu
            100                 105

<210> SEQ ID NO 11
<211> LENGTH: 97
<212> TYPE: PRT
<213> ORGANISM: Artificial Sequence
<220> FEATURE:
<223> OTHER INFORMATION: A synthetic chimeric protein

<400> SEQUENCE: 11

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Asp Asp Asp Lys Cys His
        35                  40                  45

Tyr Ala Asp Ala Ile Phe Thr Asn Ser Tyr Arg Lys Val Leu Gly Gln

```
                    50                  55                  60
Leu Ser Ala Arg Lys Leu Leu Gln Asp Ile Met Ser Arg Gln Gln Gly
 65                  70                  75                  80

Glu Ser Asn Gln Glu Arg Gly Ala Arg Ala Arg Leu Cys Ala Cys Leu
                 85                  90                  95

Glu

<210> SEQ ID NO 12
<211> LENGTH: 5
<212> TYPE: PRT
<213> ORGANISM: Artificial Sequence
<220> FEATURE:
<223> OTHER INFORMATION: A synthetic c-terminal sequence

<400> SEQUENCE: 12

Cys Ala Cys Leu Glu
 1               5

<210> SEQ ID NO 13
<211> LENGTH: 5
<212> TYPE: PRT
<213> ORGANISM: Artificial Sequence
<220> FEATURE:
<223> OTHER INFORMATION: A synthetic c-terminal sequence

<400> SEQUENCE: 13

Cys Ala Cys Asp Asp
 1               5

<210> SEQ ID NO 14
<211> LENGTH: 5
<212> TYPE: PRT
<213> ORGANISM: Artificial Sequence
<220> FEATURE:
<223> OTHER INFORMATION: A synthetic c-terminal sequence

<400> SEQUENCE: 14

Cys Ala Cys Lys Lys
 1               5

<210> SEQ ID NO 15
<211> LENGTH: 5
<212> TYPE: PRT
<213> ORGANISM: Artificial Sequence
<220> FEATURE:
<223> OTHER INFORMATION: A synthetic c-terminal sequence

<400> SEQUENCE: 15

Cys Lys Cys Leu Glu
 1               5

<210> SEQ ID NO 16
<211> LENGTH: 5
<212> TYPE: PRT
<213> ORGANISM: Artificial Sequence
<220> FEATURE:
<223> OTHER INFORMATION: A synthetic c-terminal sequence

<400> SEQUENCE: 16

Cys Ala Met Leu Glu
 1               5

<210> SEQ ID NO 17
<211> LENGTH: 5
<212> TYPE: PRT
```

```
<213> ORGANISM: Artificial Sequence
<220> FEATURE:
<223> OTHER INFORMATION: A synthetic c-terminal sequence

<400> SEQUENCE: 17

Cys Ala His Leu Glu
 1               5

<210> SEQ ID NO 18
<211> LENGTH: 97
<212> TYPE: PRT
<213> ORGANISM: Artificial Sequence
<220> FEATURE:
<223> OTHER INFORMATION: A synthetic chimeric protein

<400> SEQUENCE: 18

Met Ala Ser Met Thr Gly Gly Gln Gln Met Gly Arg Gly Ser Gly Gln
 1               5                  10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Asp Asp Asp Lys Cys His
        35                  40                  45

Tyr Ala Asp Ala Ile Phe Thr Asn Ser Tyr Arg Lys Val Leu Gly Gln
    50                  55                  60

Leu Ser Ala Arg Lys Leu Leu Gln Asp Ile Met Ser Arg Gln Gln Gly
65                  70                  75                  80

Glu Ser Asn Gln Glu Arg Gly Ala Arg Ala Arg Leu Cys Ala Cys Asp
                85                  90                  95

Asp

<210> SEQ ID NO 19
<211> LENGTH: 97
<212> TYPE: PRT
<213> ORGANISM: Artificial Sequence
<220> FEATURE:
<223> OTHER INFORMATION: A synthetic chimeric protein

<400> SEQUENCE: 19

Met Ala Ser Met Thr Gly Gly Gln Gln Met Gly Arg Gly Ser Gly Gln
 1               5                  10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Asp Asp Asp Lys Cys His
        35                  40                  45

Tyr Ala Asp Ala Ile Phe Thr Asn Ser Tyr Arg Lys Val Leu Gly Gln
    50                  55                  60

Leu Ser Ala Arg Lys Leu Leu Gln Asp Ile Met Ser Arg Gln Gln Gly
65                  70                  75                  80

Glu Ser Asn Gln Glu Arg Gly Ala Arg Ala Arg Leu Cys Ala Cys Lys
                85                  90                  95

Lys

<210> SEQ ID NO 20
<211> LENGTH: 97
<212> TYPE: PRT
<213> ORGANISM: Artificial Sequence
<220> FEATURE:
<223> OTHER INFORMATION: A synthetic chimeric protein

<400> SEQUENCE: 20
```

```
Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Asp Asp Asp Lys Cys His
        35                  40                  45

Tyr Ala Asp Ala Ile Phe Thr Asn Ser Tyr Arg Lys Val Leu Gly Gln
    50                  55                  60

Leu Ser Ala Arg Lys Leu Leu Gln Asp Ile Met Ser Arg Gln Gln Gly
65                  70                  75                  80

Glu Ser Asn Gln Glu Arg Gly Ala Arg Ala Arg Leu Cys Ala Met Leu
                85                  90                  95

Glu
```

<210> SEQ ID NO 21
<211> LENGTH: 97
<212> TYPE: PRT
<213> ORGANISM: Artificial Sequence
<220> FEATURE:
<223> OTHER INFORMATION: A synthetic chimeric protein

<400> SEQUENCE: 21

```
Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Asp Asp Asp Lys Cys His
        35                  40                  45

Tyr Ala Asp Ala Ile Phe Thr Asn Ser Tyr Arg Lys Val Leu Gly Gln
    50                  55                  60

Leu Ser Ala Arg Lys Leu Leu Gln Asp Ile Met Ser Arg Gln Gln Gly
65                  70                  75                  80

Glu Ser Asn Gln Glu Arg Gly Ala Arg Ala Arg Leu Cys Ala His Leu
                85                  90                  95

Glu
```

<210> SEQ ID NO 22
<211> LENGTH: 97
<212> TYPE: PRT
<213> ORGANISM: Artificial Sequence
<220> FEATURE:
<223> OTHER INFORMATION: A synthetic chimeric protein

<400> SEQUENCE: 22

```
Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Asp Asp Asp Lys Cys His
        35                  40                  45

Tyr Ala Asp Ala Ile Phe Thr Asn Ser Tyr Arg Lys Val Leu Gly Gln
    50                  55                  60

Leu Ser Ala Arg Lys Leu Leu Gln Asp Ile Met Ser Arg Gln Gln Gly
65                  70                  75                  80

Glu Ser Asn Gln Glu Arg Gly Ala Arg Ala Arg Leu Cys Gly His Leu
                85                  90                  95

Glu
```

<210> SEQ ID NO 23
<211> LENGTH: 97
<212> TYPE: PRT
<213> ORGANISM: Artificial Sequence
<220> FEATURE:
<223> OTHER INFORMATION: A synthetic chimeric protein

<400> SEQUENCE: 23

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Asp Asp Asp Lys Cys His
        35                  40                  45

Tyr Ala Asp Ala Ile Phe Thr Asn Ser Tyr Arg Lys Val Leu Gly Gln
    50                  55                  60

Leu Ser Ala Arg Lys Leu Leu Gln Asp Ile Met Ser Arg Gln Gln Gly
65                  70                  75                  80

Glu Ser Asn Gln Glu Arg Gly Ala Arg Ala Arg Leu Cys Leu His Leu
                85                  90                  95

Glu

<210> SEQ ID NO 24
<211> LENGTH: 5
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1
<223> OTHER INFORMATION: Ala is a dehydroalanyl

<400> SEQUENCE: 24

Ala Ala Cys Leu Glu
1               5

<210> SEQ ID NO 25
<211> LENGTH: 95
<212> TYPE: PRT
<213> ORGANISM: Artificial Sequence
<220> FEATURE:
<223> OTHER INFORMATION: A synthetic chimeric protein
<220> FEATURE:
<221> NAME/KEY: SITE
<222> LOCATION: 94
<223> OTHER INFORMATION: Xaa = any amino acid
<220> FEATURE:
<221> NAME/KEY: SITE
<222> LOCATION: 95
<223> OTHER INFORMATION: Xaa = Cys, His, or Met

<400> SEQUENCE: 25

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Asp Asp Asp Lys Cys His
        35                  40                  45

Tyr Ala Asp Ala Ile Phe Thr Asn Ser Tyr Arg Lys Val Leu Gly Gln
    50                  55                  60

Leu Ser Ala Arg Lys Leu Leu Gln Asp Ile Met Ser Arg Gln Gln Gly

```
65                  70                  75                  80
Glu Ser Asn Gln Glu Arg Gly Ala Arg Ala Arg Leu Cys Xaa Xaa
                85                  90                  95

<210> SEQ ID NO 26
<211> LENGTH: 49
<212> TYPE: PRT
<213> ORGANISM: Artificial Sequence
<220> FEATURE:
<223> OTHER INFORMATION: A synthetic precursor protein

<400> SEQUENCE: 26

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu Cys Ala Cys Leu
        35                  40                  45

Glu

<210> SEQ ID NO 27
<211> LENGTH: 49
<212> TYPE: PRT
<213> ORGANISM: Artificial Sequence
<220> FEATURE:
<223> OTHER INFORMATION: A synthetic precursor protein

<400> SEQUENCE: 27

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu Cys Ala Cys Asp
        35                  40                  45

Asp

<210> SEQ ID NO 28
<211> LENGTH: 49
<212> TYPE: PRT
<213> ORGANISM: Artificial Sequence
<220> FEATURE:
<223> OTHER INFORMATION: A synthetic precursor protein

<400> SEQUENCE: 28

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu Cys Ala Cys Lys
        35                  40                  45

Lys

<210> SEQ ID NO 29
<211> LENGTH: 49
<212> TYPE: PRT
<213> ORGANISM: Artificial Sequence
<220> FEATURE:
<223> OTHER INFORMATION: A synthetic precursor protein

<400> SEQUENCE: 29

Tyr Ala Asp Ala Ile Phe Thr Asn Ser Tyr Arg Lys Val Leu Gly Gln
```

```
                1               5                  10                 15
Leu Ser Ala Arg Lys Leu Leu Gln Asp Ile Met Ser Arg Gln Gln Gly
                20                  25                  30

Glu Ser Asn Gln Glu Arg Gly Ala Arg Ala Arg Leu Cys Ala Met Leu
        35                  40                  45

Glu

<210> SEQ ID NO 30
<211> LENGTH: 49
<212> TYPE: PRT
<213> ORGANISM: Artificial Sequence
<220> FEATURE:
<223> OTHER INFORMATION: A synthetic precursor protein

<400> SEQUENCE: 30

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
                20                  25                  30

Glu Ser Asn Gln Glu Arg Gly Ala Arg Ala Arg Leu Cys Ala His Leu
        35                  40                  45

Glu

<210> SEQ ID NO 31
<211> LENGTH: 49
<212> TYPE: PRT
<213> ORGANISM: Artificial Sequence
<220> FEATURE:
<223> OTHER INFORMATION: A synthetic precursor protein

<400> SEQUENCE: 31

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
                20                  25                  30

Glu Ser Asn Gln Glu Arg Gly Ala Arg Ala Arg Leu Cys Gly His Leu
        35                  40                  45

Glu

<210> SEQ ID NO 32
<211> LENGTH: 49
<212> TYPE: PRT
<213> ORGANISM: Artificial Sequence
<220> FEATURE:
<223> OTHER INFORMATION: A synthetic precursor protein

<400> SEQUENCE: 32

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
                20                  25                  30

Glu Ser Asn Gln Glu Arg Gly Ala Arg Ala Arg Leu Cys Leu His Leu
        35                  40                  45

Glu

<210> SEQ ID NO 33
<211> LENGTH: 5
<212> TYPE: PRT
<213> ORGANISM: Artificial Sequence
<220> FEATURE:
```

<223> OTHER INFORMATION: A synthetic peptide

<400> SEQUENCE: 33

Cys Leu His Leu Glu
1               5

<210> SEQ ID NO 34
<211> LENGTH: 5
<212> TYPE: PRT
<213> ORGANISM: Artificial Sequence
<220> FEATURE:
<223> OTHER INFORMATION: A synthetic peptide

<400> SEQUENCE: 34

Cys Gly His Leu Glu
1               5

<210> SEQ ID NO 35
<211> LENGTH: 49
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 45
<223> OTHER INFORMATION: Ala is a dehydroalanyl

<400> SEQUENCE: 35

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu Ala Ala Cys Leu
        35                  40                  45

Glu

<210> SEQ ID NO 36
<211> LENGTH: 4
<212> TYPE: PRT
<213> ORGANISM: Artificial Sequence
<220> FEATURE:
<223> OTHER INFORMATION: A synthetic peptide

<400> SEQUENCE: 36

Asp Asp Asp Asp
 1

<210> SEQ ID NO 37
<211> LENGTH: 4
<212> TYPE: PRT
<213> ORGANISM: Artificial Sequence
<220> FEATURE:
<223> OTHER INFORMATION: A synthetic peptide

<400> SEQUENCE: 37

Asp Asp Asp Lys
 1

<210> SEQ ID NO 38
<211> LENGTH: 4
<212> TYPE: PRT
<213> ORGANISM: Artificial Sequence
<220> FEATURE:
<223> OTHER INFORMATION: A synthetic peptide

```
<400> SEQUENCE: 38

Asp Thr Arg Leu
 1

<210> SEQ ID NO 39
<211> LENGTH: 4
<212> TYPE: PRT
<213> ORGANISM: Artificial Sequence
<220> FEATURE:
<223> OTHER INFORMATION: A synthetic peptide

<400> SEQUENCE: 39

Gly Gly Pro Arg
 1

<210> SEQ ID NO 40
<211> LENGTH: 97
<212> TYPE: PRT
<213> ORGANISM: Artificial Sequence
<220> FEATURE:
<223> OTHER INFORMATION: A synthetic chimeric protein

<400> SEQUENCE: 40

Met Ala Ser Met Thr Gly Gly Gln Gln Met Gly Arg Gly Ser Gly Gln
 1               5                  10                  15

Gly Gln Ala Gln Tyr Leu Ala Ala Ser Leu Val Val Phe Thr Asn Tyr
             20                  25                  30

Ser Gly Asp Thr Ala Ser Gln Val Asp Asp Asp Asp Lys Cys His
         35                  40                  45

Tyr Ala Asp Ala Ile Phe Thr Asn Ser Tyr Arg Lys Val Leu Gly Gln
     50                  55                  60

Leu Ser Ala Arg Lys Leu Leu Gln Asp Ile Met Ser Arg Gln Gln Gly
 65                  70                  75                  80

Glu Ser Asn Gln Glu Arg Gly Ala Arg Ala Arg Leu Cys Ala Cys Asp
                 85                  90                  95

Glu

<210> SEQ ID NO 41
<211> LENGTH: 97
<212> TYPE: PRT
<213> ORGANISM: Artificial Sequence
<220> FEATURE:
<223> OTHER INFORMATION: A synthetic chimeric protein

<400> SEQUENCE: 41

Met Ala Ser Met Thr Gly Gly Gln Gln Met Gly Arg Gly Ser Gly Gln
 1               5                  10                  15

Gly Gln Ala Gln Tyr Leu Ala Ala Ser Leu Val Val Phe Thr Asn Tyr
             20                  25                  30

Ser Gly Asp Thr Ala Ser Gln Val Asp Asp Asp Asp Lys Cys His
         35                  40                  45

Tyr Ala Asp Ala Ile Phe Thr Asn Ser Tyr Arg Lys Val Leu Gly Gln
     50                  55                  60

Leu Ser Ala Arg Lys Leu Leu Gln Asp Ile Met Ser Arg Gln Gln Gly
 65                  70                  75                  80

Glu Ser Asn Gln Glu Arg Gly Ala Arg Ala Arg Leu Cys Lys Cys Leu
                 85                  90                  95

Glu
```

-continued

```
<210> SEQ ID NO 42
<211> LENGTH: 5
<212> TYPE: PRT
<213> ORGANISM: Artificial Sequence
<220> FEATURE:
<223> OTHER INFORMATION: A synthetic peptide

<400> SEQUENCE: 42

Cys Ala Cys Asp Glu
 1               5

<210> SEQ ID NO 43
<211> LENGTH: 40
<212> TYPE: PRT
<213> ORGANISM: Artificial Sequence
<220> FEATURE:
<223> OTHER INFORMATION: A synthetic chimeric protein
<220> FEATURE:
<221> NAME/KEY: SITE
<222> LOCATION: 31-40
<223> OTHER INFORMATION: Xaa = any amino acid

<400> SEQUENCE: 43

Met Val Asp Asp Asp Asn Gly Lys Leu Ser Gln Glu Leu His Lys
 1               5                  10                  15

Leu Gln Thr Tyr Pro Arg Thr Asp Val Gly Ala Gly Thr Pro Xaa Xaa
             20                  25                  30

Xaa Xaa Xaa Xaa Xaa Xaa Xaa Xaa
             35                  40
```

PEPTIDE AMIDATION PROCESS

CROSS-REFERENCE TO RELATED APPLICATIONS

This application is a continuation under 35 U.S.C. 111(a) of PCT/US03/16648, filed on May 23, 2003 and published on Dec. 4, 2003 as WO 03/099853 A2, which claims priority under 35 U.S.C 119(e) of U.S. Provisional Application No. 60/383,362, filed on May 24, 2002, which applications and publication are incorporated herein by reference.

FIELD OF THE INVENTION

The invention provides a novel one-step polypeptide cleavage and amidation process in which the polypeptide is cleaved and amidated by solubilization in reaction media comprising a palladium promotor and an organic acid. When employed commercially, the invention provides an economic and efficient means to produce a biologically active peptide.

BACKGROUND OF THE INVENTION

Two significant problems are encountered in recombinant peptide expression. First, many biologically active peptides have an amide at their C-terminus. Such amidated peptides are not typically produced through recombinant expression. Second, C-terminal amide group substitution, performed routinely in vivo, proves difficult to perform in vitro.

It is well known that the production of short and medium range peptides of less than about 100 amino acids in length by expression of peptide-encoding DNA in a recombinant host cell such as *E. coli* is commonly plagued by the problem of enzymatic degradation of the expressed peptide within the host cell, resulting in partial or complete loss of the peptide. The most commonly employed means to overcome this problem is to insolubilize the peptide within the host cell. This can be affected by expressing the peptide as a chimeric protein in which the peptide is linked to a fusion partner. Normally, the fusion partner will be fused to the N-terminus of the peptide. The chimeric protein forms inclusion bodies within the cell, within which the peptide is protected from degradation by proteolytic enzymes.

Once the inclusion bodies are recovered from the host cell, the peptide must be separated from the leader sequence, purified and recovered in an active form. Separation from the leader sequence may be accomplished by placing a sequence of amino acids at the junction of the leader and the peptide which are specifically recognized and cleaved under appropriate conditions, e.g. acid cleavage or enzymatic cleavage.

For example, introduction of acid-labile aspartyl-proline linkage between the two segments of a chimeric protein facilitates their separation at low pH. The major requirement of this system is that the desired segment of interest is not acid-labile. Chimeric proteins comprising hormones such as insulin and somatostatin have been cleaved with cyanogen bromide, which is specific for the carboxyl side of methionine residues, to release the desired hormone. This method is not suitable when the desired protein contains methionine residues.

Cleavage of chimeric proteins by site-specific proteolysis has also been investigated. Chimeric proteins into which a chicken pro alpha-2 collagen linker was inserted could be specifically degraded by purified microbial collagenase to release the components of the chimeric protein. Use of proteolytic enzymes to cleave the chimeric protein has drawbacks because the enzymes can be expensive, the yield of product is frequently low, and it can prove difficult to later separate the enzyme (a protein) from a desired cleavage product. Other methods for purification and recovery of a desired recombinant protein include construction of a poly-arginine tail at the carboxyterminus of the protein. The arginine residues increase the overall basicity of the protein which facilitates purification of the desired protein by ion exchange chromatography. Subsequent removal of the poly-arginine tail by carboxypeptidase B regenerates the desired protein and allows purification from basic contaminants due to the reduction in pI of the desired protein.

Acid cleavage can be accomplished by placing a specific dipeptide at the junction of the leader sequence and the peptide. Selection of the second amino acid will determine the rate at which the dipeptide bond is cleaved under acidic conditions. Of course, if the desired peptide contains any internal dipeptide sequences that are acid cleavable, then the cleavage site at the junction of the leader and the peptide must undergo acid cleavage at a substantially greater rate than the internal cleavage in order to avoid unacceptable loss of yield.

In addition to difficulties encountered with chimeric protein cleavage, natural amino acid modifications such as C-terminal amide group substitution, performed routinely in vivo, are difficult to perform in vitro. These post-translational modifications often result in the most potent or longest acting form of a peptide and render the peptide most suitable for pharmaceutical use. For many peptides, C-terminal amidation is important for biological activity. However, recombinant expression systems for large scale production of active peptides cannot easily carry out the necessary C-terminal modification.

Carboxypeptidase enzymes are known to catalyze transpeptidation reactions, yielding C-terminally amidated peptides. However, wild type carboxypeptidase enzymes are not useful for C-terminal amidation of many peptides. For example, the inherent substrate specificity of wild-type carboxypeptidase restricts the variety of peptides that may be modified using this enzyme. Transpeptidation occurs when an amino acid or amino acid derivative acts as a leaving group and the nucleophile is an amino acid, or amino acid derivative, such as an amino acid ester or amino acid amide. "Transamidation" includes transpeptidation, in that an amide bond is formed between the nucleophile and the peptide substrate. However, in a transamidation reaction, the nucleophile is not necessarily an amino acid.

In particular, carboxypeptidase Y displays a strong preference for peptides with a penultimate apolar residue. Substrates having a penultimate amino acid with a positively charged side chain are not effectively hydrolyzed nor transacylated by carboxypeptidase Y. For example, the substrate FA-Arg-Ala-OH (SEQ ID NO:1) is hydrolyzed about 500 times more slowly than the substrate FA-Leu-Ala-OH (SEQ ID NO:2). Unfortunately, the amino acid sequences of many pharmaceutically important peptides, including growth hormone releasing factor (GRF) or glucagon like peptide-1 (GLP-1), have a penultimate or ultimate amino acid with a positively charged side chain, making transamidation with carboxypeptidase Y commercially impractical.

U.S. Pat. No. 6,251,635 describes the treatment of a chimeric protein, including multiple copies of a target sequence, in a precursor peptide which includes hCA-MetValAspAspAspAspAsn-ECF2)$_n$-Xxx (SEQ ID NO:3), where hCA is human carbonic anhydrase, ECF2 is a polypeptide fragment having the formula: Gly-Lys-Leu-Ser-Gln-Glu-Leu-His-Lys-Leu-Gln-Thr-Tyr-Pro-Arg-Thr-Asp-Val-Gly-Ala-Gly-Thr-Pro (SEQ ID NO:4); and Xxx is typically a C-terminal carboxylic acid ("—OH"), a C-terminal carboxamide ("—NH$_2$"), or group capable of being converted into a C-terminal carboxamide, such as an amino acid residue or a polypeptide group (typically having from 2 to about 10 amino acid residues), and n is an integer (typically 2 to 20). Such a precursor peptide may be treated with CNBr to form Val-AspAspAspAspAsn-ECF2-Hse (SEQ ID NO:5) peptide fragments (where Hse is a homoserine residue produced by the reaction of CNBr with a Met residue). The peptide fragments may then be reacted with a nucleophile such as o-nitrophenylglycine amide ("ONPGA") in the presence of a peptidase such as carboxypeptidase Y resulting in the replacement of the Hse residue by ONPGA Upon photolysis, the transpeptidation product is converted to a C-terminal carboxamide. The N-terminal tail sequence, Val-AspAspAspAspAsn (SEQ ID NO:6), may be cleaved off the fragments by treatment with hydroxylamine.

Another method of forming a C-terminal amide on a recombinantly produced polypeptide uses the enzyme peptidyl alpha-amidating enzyme which is present in eukaryotic systems. The enzyme has been used to form an amide on the C-terminal amino acid of recombinantly produced peptides, like human growth hormone releasing hormone in vitro, as described by Engels, *Protein Engineering*, 1:195-199 (1987). While effective, the enzymatic method is time consuming, expensive, gives unpredictable yields, and requires significant post-reaction purification.

Patchornik and Sokolovsky, *JACS*, 86: 1206-1212 (1964) describe the reaction of peptidyldehydroalanine in acidic solution to yield an amidated peptide. It is however undesirable to employ this technique to amidate a peptide as it requires relatively harsh conditions, viz. boiling in mild acidic aqueous solution. Even in the presence of a Lewis acid catalyst such as Hg$^{2+}$, the reaction still not very successful. (Edge and Weber, *Int. J. Peptide Protein Res.*, 18: 1-5 (1981)). If the reaction substrate is treated with organic and/or inorganic acid and contains acid sensitive amino acid residues, the harsh reaction conditions will produce side products.

Thus, known polypeptide amidation processes suffer from numerous drawbacks. Such reactions may be sequence-specific, require harsh conditions and may require multiple steps for cleavage and amidation.

Accordingly, there is a need for an improved process that provides for the efficient cleavage and amidation of a peptide.

OBJECTS OF THE INVENTION

It is an object of the instant invention to provide a one-step process for the cleavage and amidation of a polypeptide, particularly a peptide that has been expressed recombinantly as a chimeric protein.

It is another object of the instant invention to provide a one-step process for the cleavage and amidation of a peptide which utilizes mild reaction conditions.

SUMMARY OF THE INVENTION

In accordance with the above stated objects, the instant invention provides a novel one-step palladium-promoted polypeptide cleavage and amidation reaction which may be applied to a variety of peptides. The reaction is particularly well-suited for use in the cleavage and amidation of peptides which have been expressed recombinantly in the form of chimeric proteins. Importantly, the process provides for amidation at the C-terminus of a polypeptide that proceeds in a manner that is independent of the specific amino acid sequence of the polypeptide C-terminus. Accordingly, the process may be used to produce a wide variety of biologically active peptides.

Generally, the invention provides a process wherein a substrate polypeptide is cleaved though palladium-promoted cleavage at a palladium recognition site formed by a bond between any amino acid and a cysteine. This cleavage reaction produces a product polypeptide having an amidated C-terminus and a tail sequence having an amino-terminal cysteine. It has been discovered that the reaction can be regulated through alteration of the palladium recognition site by placement of specific amino acids on the carboxyl-side of the cysteine on the tail sequence. This palladium recognition site can be represented by Cys-$X_2$-$X_3$, wherein $X_2$ can be any amino acid, and $X_3$ is selected from Cys, His, or Met. Thus, it is possible to design substrate polypeptides that can be cleaved by palladium to produce a desired product polypeptide having an amidated C-terminus. For example, a substrate polypeptide can be represented as follows: (desired polypeptide-$X_1$)-(Cys-$X_2$-$X_3$-tail sequence), wherein $X_1$ and $X_2$ can be any amino acid, and $X_3$ is selected from Cys, His, or Met. Cleavage of this substrate polypeptide according to the invention will produce the following: (desired polypeptide-$X_1$-NH$_2$) and (Cys-$X_2$-$X_3$-tail sequence).

In another embodiment, the process of the invention can be used to cleave a substrate polypeptide at more than one palladium recognition site. For example, a substrate polypeptide can be represented as follows: (leader polypeptide-Cys-His)-(desired polypeptide-$X_1$)-(Cys-$X_2$-$X_3$-tail sequence), wherein $X_1$ and $X_2$ can be any amino acid, and $X_3$ is selected from Cys, His, or Met. Cleavage of this substrate polypeptide according to the invention will produce the following: (leader polypeptide-Cys-His) and (desired polypeptide-$X_1$-NH$_2$) and (Cys-$X_2$-$X_3$-tail sequence). Thus, the process of the invention can be used to cleave a substrate polypeptide to produce a desired polypeptide having an amidated C-terminus. The process of the invention can also be used to cleave multimeric substrate polypeptides to produce numerous desired polypeptides that have an amidated C-termini from a single substrate polypeptide. Many recognition sites for palladium cleavage can be used to prepare a substrate polypeptide. Examples of such recognition sites are provided herein. A substrate polypeptide can be cleaved and amidated in the process of the instant invention by reacting the polypeptide in a reaction mixture of an acidic organic solvent and a palladium promotor, wherein the concentration of the organic acid solvent is between about 1 to about 6 molar.

In an embodiment of the instant invention in which a polypeptide is cleaved at a cleavage site which links the N-terminus of a first amino acid sequence defining the peptide to a second amino acid sequence defining a leader sequence, such cleavage site can include Cys-His-, Asn-Gly-, -Met-, -Asp-Pro, -Arg-, DDDDK (SEQ ID NO:7) or -GGGGPR (SEQ ID NO:8). The polypeptide tail sequence—Cys-$X_2$-$X_3$ may be amidated either concurrently with, or independent of, any polypeptide leader-sequence cleavage reaction.

The process of the invention can be used to cleave naturally occurring polypeptides having a suitable amino acid sequence. The process of the invention can also be used to cleave synthetic, or recombinantly produced polypeptides.

BRIEF DESCRIPTION OF THE DRAWINGS

FIG. 1 illustrates the DNA (SEQ ID NO:9) and peptide (SEQ ID NO:10) sequence of the GRF chimeric protein.

FIG. 3 illustrates the HPLC-MS analysis of the reaction products of T7tag-Vg-D$_4$KCH-GRF(1-44)CACLE (SEQ ID NO:11) with tetrachloropalladate in malonic acid.

DETAILED DESCRIPTION OF THE INVENTION

Figure 2:
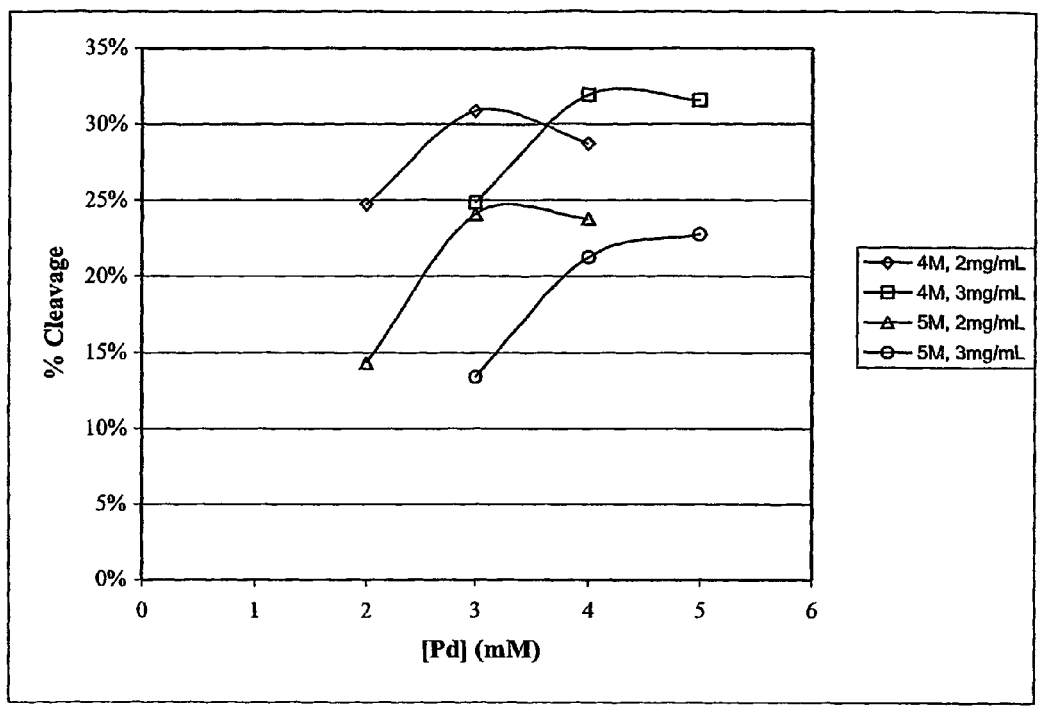
FIG. 2 illustrates the yield of amidated GRF obtained using T7tag-Vg-D$_4$KCH-GRF(1-44)CACLE (SEQ ID NO:11) at various palladium promotor and malonic acid concentrations.

The instant invention may be employed to amidate naturally occurring, synthetically-derived or recombinantly expressed polypeptides. In the embodiments illustrated in detail hereinafter, the invention is employed to amidate recombinantly expressed chimeric proteins that have been recovered from host cells in the form of inclusion bodies.

Chimeric proteins employed in the instant invention may be expressed in a microbial host cell using known techniques of recombinant DNA production. Any suitable host cell known to be useful for the expression of proteins by recombinant DNA methods may be employed, including prokaryotic and eukaryotic host cells and cell lines. *E. coli* is a preferred host cell. The host cell contains an expression vector which encodes the chimeric protein under the control of a regulatory sequence which is capable of directing its expression in the host, as well as an origin of replication that is functional in the host cell. The vector may contain other DNA sequences conventionally employed in recombinant DNA technology such as sequences encoding selectable markers. Methods for expressing a foreign gene in a host organism also are well known in the art (see, e.g., Maniatis et al. *Molecular Cloning: A Laboratory Manual*, Cold Spring Harbor Laboratory Press, 2$^{nd}$ ed., 1989).

The gene encoding a particular polypeptide can be constructed by chemically synthesizing the entire nucleotide sequence, by amplification, such as by the polymerase chain reaction (PCR), or by cloning the gene of interest. The gene is then subcloned into an appropriate expression vector. Cloning vectors, expression vectors, plasmids, and viral vectors are well known in the art (see, e.g., Maniatis et al., supra, and Goedell, *Methods in Enzymology*, Vol. 185 (Academic Press 1990)). Example 1 provides a detailed description of the preparation of a T7-based expression system useful for high-level expression of mammalian proteins in *E. coli*.

The host cell containing the expression vector is grown and the chimeric protein expressed under appropriate conditions. The conditions for growth of the host cell and expression of the chimeric protein will vary depending on various factors such as the host cell employed, the promoter and the particular chimeric protein being expressed. Those skilled in the art are capable of determining the appropriate conditions for the particular host/vector system employed. Methods for expressing a foreign gene in a host organism also are well known in the art (see, e.g., Maniatis et al., *Molecular Cloning: A Laboratory Manual*, Cold Spring Harbor Laboratory Press, 2$^{nd}$ ed., 1989). The gene encoding a particular polypeptide can be constructed by chemically synthesizing the entire nucleotide sequence, by amplification, such as by the polymerase chain reaction (PCR), or by cloning the gene of interest. The gene is then subcloned into an appropriate expression vector. Cloning vectors, expression vectors, plasmids, and viral vectors are well known in the art (see, e.g., Maniatis et al., supra, and Goedell, *Methods in Enzymology*, Vol. 185 (Academic Press 1990)). Example 1 provides a detailed description of the preparation of a T7-based expression system useful for high-level expression of mammalian proteins in *E. coli*.

When a polypeptide is prepared by recombinant techniques, one can add a cleavage site at a point preceding the N-terminus, and a Cys-X$_2$-X$_3$ tail sequence to the C terminus of the amino acid sequence defining the peptide product, by incorporating or mutating the appropriate nucleotides into the encoding nucleic acid by any of various methods including, for example, site-directed mutagenesis. Such cleavage site and Cys-X$_2$-X$_3$ sequences can provide a site for concurrent cleavage and amidation by palladium complexes as described herein. Recombinant methods can also be used to generate a nucleic acid encoding a protein with a repeating polypeptide sequence, with each sequence separated by a predetermined cleavage site and the C-terminus of each sequence attached to the group Cys-X$_2$-X$_3$. In this case, palladium complex-promoted concurrent cleavage and amidation can occur at multiple cleavage sites as defined above in the polypeptide, releasing multiple copies of the desired peptide.

As used herein, "protein," "polypeptide," and "peptide" are used interchangeably and are intended to refer to any sequence of two or more amino acids, regardless of length, and including those having a molecular weight of between about 400 to about 100,000 daltons or greater (preferably between 1,000 and 50,000 daltons). Polypeptides suitable for cleavage can comprise any of the natural amino acids, such as Ala (A), Arg (R), Asp (D), Asn (N), Glu (E), Gln (O), Gly (G), His (H), Leu (L), Ile (I), Lys (K), Met (M), Cys (C), Phe (F), Pro (P), Ser (S), Thr (T), Trp (W), Tyr (Y), Val (V) (single letter amino acid code in parentheses), or may comprise any side chain-modified amino acid derivative commonly used in peptide chemistry. The latter amino acid derivatives include, for example, 1- or 2-napthylalanines and p-benzoylamino-L-phenylalanine, among others.

The process of the instant invention is applicable to natural polypeptides, synthetic polypeptides, or polypeptides produced using recombinant techniques. Methods for preparing synthetic polypeptides are well known in the art and include, for example, Merrifield solid phase peptide synthesis. Methods for expressing a foreign gene in a host organism also are well known in the art (see, e.g., Maniatis et al. *Molecular Cloning: A Laboratory Manual*, Cold Spring Harbor Laboratory Press, 2$^{nd}$ ed., 1989). The gene encoding a particular polypeptide can be constructed by chemically synthesizing the entire nucleotide sequence, by amplification, such as by the polymerase chain reaction (PCR), or by cloning the gene of interest. The gene is then subcloned into an appropriate expression vector. Cloning vectors, expression vectors, plasmids, and viral vectors are well known in the art (see, e.g., Maniatis et al., supra, and Goedell, *Methods in Enzymology*, Vol. 185 (Academic Press 1990)). Example 1 provides a detailed description of the preparation of a T7-based expression system useful for high-level expression of mammalian proteins in *E. coli*.

Thus, the process of the instant invention provides for the production of desired peptides which include, but are not limited to, glucagon-like peptide-2 (GLP-2), glucagon-like peptide-1 (GLP-1), growth hormone-releasing factor (GRF), parathyroid hormone (PTH), parathyroid hormone related peptide, adrenocorticotropic hormone (ACTH), enkephalins, endorphins, exendens, amylins, various opioid peptides, frog skin antibiotic peptides, such as gaegurins 5 and 6, brevinin 1, the ranatuerins 1 through 9, and the esculetins, glucose-dependent insulinotropic polypeptide (GIP), glucagon, motilin, thymopoietins, thymosins, ubiquitin, serum thymic factor, thymic humoral factor, neurotensin, tuftsin, and fragments and derivatives of these peptides.

Precursor non-amidated or reduced forms of the following peptides and other peptides of like nature, can also be expressed as a fusion construct with a predetermined cleavage site and subjected to cleavage and concurrent or sequential amidation in accordance with the process of the instant invention: gastrin, calcitonin, luteinizing-hormone-releasing hormone, pancreatic polypeptide, endothelin, corticotropin releasing factor, neuropeptide Y, atrial naturetic peptide, amylin, galanin, somatostatins, vasoactive intestinal peptide, insulin, and fragments and derivatives of these peptides.

Examples of leader sequences which can be employed with chimeric proteins include a signal sequence such as that used to direct secretion of a protein from a cell, the N-terminal portion of a mature protein sequence, such as from a structural gene, a linker sequence, or combinations thereof. Useful leader sequences also are shown in Example 1. A leader sequence can be obtained from the genes encoding glutathione-S-transferase or carbonic anhydrase. Linkers may be designed to end in a predetermined cleavage sequences. C-Terminal sequences which may be employed in accordance with the process of the instant invention include any sequence defined by Cys-$X_2$-$X_3$, where $X_2$ is any amino acid and $X_3$ is Cys, His, or Met. Such sequences include, but are not limited to, CACLE (SEQ ID NO:12), CACDD (SEQ ID NO:13), CACKK (SEQ ID NO:14), CKCLE (SEQ ID NO:15), CAMLE (SEQ ID NO:16), and CAHLE (SEQ ID NO:17).

In preferred embodiments of the instant invention in which the peptide has been expressed in the form of a chimeric protein, the chimeric protein has a molecular weight of between about 400 to about 100,000 daltons or greater (preferably between 1,000 and 50,000 daltons and can comprise any of the natural amino acids, such as Ala (A), Arg (R), Asp (D), Asn (N), Glu (E), Gln (O), Gly (G), His (H), Leu (L), Ile (I), Lys (K), Met (M), Cys (C), Phe (F), Pro (P), Ser (S), Thr (T), Trp (W), Tyr (Y), Val (V) (single letter amino acid code in parentheses), or may comprise any side chain-modified amino acid derivative commonly used in peptide chemistry. The latter amino acid derivatives include, for example, 1- or 2-napthylalanines and p-benzoylamino-L-phenylalanine, among others.

After the chimeric protein has been expressed it can be recovered (in the form of inclusion bodies) from the host cells by known methods such as, for example, lysing the cells chemically or mechanically and separating the inclusion bodies (chimeric protein) by centrifugation. Recovered inclusion bodies are thereafter subjected to palladium-promoted hydrolytic cleavage by dissolving them in a reaction mixture comprising 1 to about 22 molar organic acid containing a palladium (II) or (IV) complex (e.g., tetrachloropalladate(II)). The palladium complex is added in significant molar excess to the chimeric protein in the process of the instant invention, ideally in about 2- to about 20-fold molar excess (preferably in about 5:1 molar excess over Cys). The organic acid can include monocarboxylic acids such as acetic acid, propionic acid, butyric acid, pyruvic acid; hydroxysubstituted acids such as lactic acid, tartaric acid, citric acid; dicarboxylic acids such as oxalic acid, malic acid, maleic acid, malonic acid, fumaric acid, glutaric acid, adipic acid, succinic acid, pimelic acid; tricarboxylic acids such as tricarballylic acid; sugar acids such as glucuronic acid and other uronic acids, aldonic acids such as gluconic acid; and aldaric acids such as saccharic acid.

Acetic, citric, formic, maleic, malonic, propionic, pyruvic, tartaric, lactic, and trifluoroacetic acids are preferred organic acid solvents. Cleavage is usually carried out at a temperature of between about 50° C. to about 70° C.

It is understood that the reaction conditions of the cleavage step of the process of the instant invention are adjusted depending on the palladium complex used and the characteristics of the polypeptide to be cleaved. The palladium complex should be solubilized, which will affect the reaction conditions. Moreover, in a preferred embodiment, the reaction conditions used will at least partially denature the polypeptide to be cleaved.

Palladate (Pd) (II) complexes that can promote the cleavage of polypeptides in accordance with the instant invention include $[Pd(OH_2)_3(OH)]^+$, $[PdCl_4]^{2-}$, cis-$[Pd(en)(OH_2)_2]^{2+}$, cis-$[Pd(pn)(OH_2)_2]^{2+}$, cis-$[Pd(pic)(OH_2)_2]^{2+}$, cis-$[Pd(bpy)(OH_2)_2]^{2+}$, cis-$[Pd(phen)(OH_2)_2]^{2+}$, and cis-$[Pd(dtco-OH)(OH_2)_2]^{2+}$. Additionally, Pd (IV) complexed with chloride ion as hexachloropalladate can also provide an effective cleavage agent. Palladium complexes can be prepared by methods well known in the art (see e.g., (Hohmann et al., *Inorg. Chim. Acta*, 174: 87 (1990); Rau et al., *Inorg. Chem.*, 36: 1454 (1997); Drexler et al., *Inorg. Chem.*, 30: 1297 (1991), or U.S. Pat. No. 5,352,771) or can be purchased commercially. Preferred palladium complexes include salts of the following: $[PdCl_4]^{2-}$, $[Pd(NCCH_3)_2(OH_2)_2]^{2+}$, and $[PdCl_6]^{2-}$. Palladium complexes most preferred include $[PdCl_4]^{2-}$, $[Pd(NCCH_3)(OH_2)_2]^{2+}$, and $[PdCl_6]^{2}$ Complexes are used as the salt of an inorganic base, such as sodium or potassium. The sodium salt of $[PdCl_4]^{2-}$ is preferred.

In one embodiment of the instant invention, the chimeric protein (in the form of a precursor peptide) T7tag-Vg-$D_4$KCH-GRF(1-44)CACLE (SEQ ID NO:11) was expressed in *E. coli* and thereafter concurrently cleaved and amidated in accordance with the process of the instant invention. This chimeric protein has a leader sequence connected by a Cys-His sequence to the growth hormone releasing factor peptide GRF(1-44). The GRF is linked to a Cys-Ala-Cys-Leu-Glu (SEQ ID NO:12) C-terminal sequence. The precursor peptide comprises a 14-residue signal sequence followed by both a 27 residue vestigial (Vg) sequence (which induced inclusion body formation and high expression) and a 13-residue linker which ends with the Cys-His cleavage site. The precursor peptide was reacted in a mixture of (1) 4 M malonic acid in a ratio of 3 mg of precursor peptide/mL malonic acid, and (2) 4mM $Na_2PdCl_4$ The reaction proceeded at about 60° C. for approximately 2 hours to yield around 17-21% of amidated peptide product as determined by HPLC analyses.

Other precursor peptides which have been cleaved and amidated in accordance with the process of the instant invention include:

| | |
|---|---|
| $T_7$-Vg-$D_4$KCH-GRF (1-44)-CACLE; | (SEQ ID NO:11) |
| $T_7$-Vg-$D_4$KCH-GRF (1-44)-CACDD; | (SEQ ID NO:18) |
| $T_7$-Vg-$D_4$KCH-GRF (1-44)-CACKK; | (SEQ ID NO:19) |
| $T_7$-Vg-$D_4$KCH-GRF (1-44)-CAMLE; | (SEQ ID NO:20) |
| $T_7$-Vg-$D_4$KCH-GRF (1-44)-CABLE; | (SEQ ID NO:21) |
| $T_7$-Vg-$D_4$KCH-GRF (1-44)-CGHLE; | (SEQ ID NO:22) | and

| | |
|---|---|
| $T_7$-Vg-$D_4$KCH-GRF (1-44)-CLHLE; | (SEQ ID NO:23) |

These precursor peptides were cleaved and amidated using 5 M malonic acid as an organic solvent, at precursor peptide concentration ranges of approximately 2 mg of precursor peptide/mL of organic solvent, with Pd (II) promoter concentrations of 5.6 molar excess to Cys, at a reaction temperature of about 60° C. and a reaction time of about 2 hours. Cleavage and amidation yields for these various precursor peptides obtained under these conditions ranged from 2 to 50%.

The mechanistic pathway for conversion of the Cys-$X_2$-$X_3$ tail sequence to the amidated GRF product is not known. Without intending any limitation to the scope of the instant invention, one possible explanation is that the first Cys (i.e., Cys) moiety is converted to dehydroalanine to give a JACLE (SEQ ID NO:24) species (where J is used as the single letter code for the dehydroalanyl residue). The dehydroalanine group then is either oxidatively or hydrolytically cleaved (most likely with Pd assistance) at the amino terminal side to leave GRF in amidated form.

Other embodiments of the instant invention are disclosed in the following Examples, which are illustrative and not limiting.

EXAMPLE 1

Expression of T7tag-Vg-$D_4$KCH-GRF (1-44)-Cys-$X_2$-$X_3$ (SEQ ID NO:25) Precursor Peptides:

The following precursor peptides:

```
T7tag-Vg-D4KCH-GRF (1-44)-CACLE;    (SEQ ID NO:11)

T7tag-Vg-D4KCH-GRF (1-44)-CACDD;    (SEQ ID NO:18)

T7tag-Vg-D4KCH-GRF (1-44)-CACKK;    (SEQ ID NO:19)

T7tag-Vg-D4KCH-GRF (1-44)-CAMLE;    (SEQ ID NO:20)

T7tag-Vg-D4KCH-GRF (1-44)-CAHLE;    (SEQ ID NO:21)

T7tag-Vg-D4KCH-GRF (1-44)-CGHLE;    (SEQ ID NO:22)

and

T7tag-Vg-D4KCH-GRF (1-44)-CLHLE;    (SEQ ID NO:23)
``` were recombinantly expressed in *E. Coli* as follows.

*E. Coli* bacteria containing expression plasmids encoding the T7tag-Vg-$D_4$K-CH-GRF(1-44)Cys-$X_2$-$X_3$ (SEQ ID NO:25) polypeptides (e.g., the T7tag-Vg-$D_4$K-CH-GRF(1-44)CACLE (SEQ ID NO:11) in FIG. 2) were grown in 500 mL shake flasks containing tryptone, yeast, glucose, batch salts (sodium and potassium mono- and diphosphate salts and ammonium sulfate), and antibiotic. Inoculated shake flasks were subject to orbital shaking (200 rpm, 37° C.). Incubation was completed when the culture reached an optical density (OD) of 0.8-1.8 at 540 nm.

Fermentors ranging from 5 L to 100 L production capacities were seeded using shake flask cultures. The media included batch salts, glucose, and chelated metals solution (potassium citrate, sodium citrate, magnesium sulfate, phosphoric acid ferric chloride, zinc chloride, cobalt chloride, sodium molybdate, manganese chloride, calcium chloride, and copper sulfate). The pH of the medium was adjusted to 6.9 prior to inoculation and the pH was maintained at 6.9 during culture. Dissolved oxygen was maintained at approximately 40%, via agitation and supplemental oxygen. Either silicone-based or polypropylene glycol-based "antifoam" was added aseptically on an "as needed" basis to reduce foaming in the fermentation culture.

When the fermentation culture OD reached 25 at 540 nm, recombinant protein expression was induced by adding filter-sterilized isopropylthiogalactoside (IPTG, 600 mm) to a final concentration of 0.5 mM, followed by filter-sterilized magnesium induction supplement (potassium citrate and magnesium sulfate). The culture was incubated for another 6 hr, and then cooled to 10-15° C.

EXAMPLE 2

Recovery of Inclusion Bodies of T7tag-Vg-$D_4$KCH-GRF(1-44)-Cys-$X_2$-$X_3$ (SEQ ID NO:25) Precursor Peptides The inclusion bodies prepared as in Example 1 were recovered as follows. The *E. Coli* cells from 500 mL shake flask were isolated. To the whole cells suspended in Tris-EDTA buffer (pH 8.0, 10 mM and 1 mM, respectively) was added lysozyme. Freeze-thaw process followed by sonication broke the cells. The crude precursor peptides were further purified by solubilization in 1.5 M citric acid followed by precipitation by titration of the acid with NaOH. The precipitate obtained at pH 4.0 was washed with deionized water until the conductivity of the solution became less than 0.1 mS. The residual white cake was lyophilized. The whole cells containing precursor peptides from 5 L fermentations were suspended in Tris-EDTA buffer (pH 8.0, 10 mM and 1 mM, respectively) and then pressurized to break. The isolated precursor peptide was further washed with deionized water until the conductivity of the wash became less than 0.1 mS.

The crude precursor peptides GRF-CACLE (SEQ ID NO:26), GRF-CACDD (SEQ ID NO:27), GRF-CACKK (SEQ ID NO:28), GRF-CAMLE (SEQ ID NO:29), GRF-CAHLE (SEQ ID NO:30), GRF-CGHLE (SEQ ID NO:31), and GRF-CLHLE (SEQ ID NO:32) were further purified by solubilization in 6.5 M malonic acid or 3.5 M citric acid followed by sonication (with probe sonicator, 2 mm tip OD). The precursor peptides were purified by HPLC with a Microsorb MV-100 CNC8 column (4.6×100 mm). The IBs were eluted with a linear gradient; 10-100% B in 20 min with buffers; A was 100% water and 5 mM HCl, and B 95% acetonitrile and 5 mM HCl at 0.8 mL/min of flow rate and monitored at 280 nm.

EXAMPLE 3

Analytical Methods

HPLC Method 1: Beckman HPLC with System Gold v 8.1 software, with Waters Symmetry column (4.6×150 mm with a guard column (4.6×15 mm)). A typical HPLC performance was done with a linear gradient; 20-30% B in 5 min, 30-38% B in 15 min and 38-100% B in 3 min, with buffers; A was 100% water and 0.1% TFA, and B 95% acetonitrile and 0.1% TFA.

HPLC Method 2: LC-MS: Finnigan Duo Q LC-MS with a 4.6×250 mm, 10 μm, 300 Å Vydac $C_8$ reverse phase column was used. The gradient followed the same rate of change of the organic modifier as in method 3.

HPLC Method 3: for t=0 (inclusion bodies) and reaction time-course samples (through $t_{final}$), a 4.6×250 mm, 10 μm, 300 Å Vydac $C_8$ reverse phase column was used (1 mL/min flow, 32° C. setpoint on column heater) with the following mobile phases:

A=20% acetonitrile, 0.1% TFA; B=75% acetonitrile, 0.1% TFA. The gradient used was 15-33% B (25 min.), 33-100% B (5 min.), 100-15% B (1 min.), 15% B (7 min.). UV absorbance detection was at 214 nm.

EXAMPLE 4

The Use of Citric Acid in Cleavage-amidation of T7tag-Vg-D4KCH-GRF(1-44)-CACLE (SEQ ID NO:11)

Precursor peptide, T7tag-Vg-D4KCH-GRF(1-44)-CACLE, was dissolved with homogenization in citric acid at concentrations of 1 mg/mL, 2 mg/mL, and 3 mg/mL using techniques as described in Example 2. Approximately 3.5 M citric acid stock was diluted to a 3 M final concentration during homogenization. For each inclusion body concentration, five tetrachloropalladate concentrations were investigated: 1 mM, 2 mM, 5 mM, 10 mM, and 15 mM. The reaction time was six hours and the reaction temperature was 60° C. Yields of amidated r-GRF of up to 14% were determined by HPLC Method 3 of Example 3 and are listed in Table 1.

TABLE 1

| [Precursor] | [Pd] | % Yield Amidation (average) |
|---|---|---|
| 1 mg/mL, | 1 mM Pd | 4.8 |
| 1 mg/mL, | 2 mM Pd | 14.0 |
| 1 mg/mL, | 5 mM Pd | 7.4 |
| 1 mg/mL, | 10 mM Pd | 3.5 |
| 1 mg/mL, | 15 mM Pd | 2.9 |
| 2 mg/mL, | 1 mM Pd | 1.1 |
| 2 mg/mL, | 2 mM Pd | 2.8 |
| 2 mg/mL, | 5 mM Pd | 11.0 |
| 2 mg/mL, | 10 mM Pd | 4.7 |
| 2 mg/mL, | 15 mM Pd | 2.9 |
| 3 mg/mL, | 1 mM Pd | 1.1 |
| 3 mg/mL, | 2 mM Pd | 1.0 |
| 3 mg/mL, | 5 mM Pd | 9.5 |
| 3 mg/mL, | 10 mM Pd | 6.7 |
| 3 mg/mL, | 15 mM Pd | 3.4 |

EXAMPLE 5

The Use of Malonic Acid in Cleavage-amidation of T7tag-Vg-D4KCH-GRF(1-44)-CACLE (SEQ ID NO:11)

Four solubilizations of GRF-CACLE (SEQ ID NO:26) inclusion bodies into malonic acid were made as follows: 2 mg/mL in 4 M malonic, 2 mg/mL in 5 M malonic, 3 mg/mL in 4 M malonic, and 3 mg/mL in 5 M malonic. For each of the two solutions at 2 mg/mL peptide, tetrachloropalladate was introduced at 2, 3, and 4 mM concentrations. For the two 3 mg/mL solutions, tetrachloropalladate was added separately at 3, 4, and 5 mM concentrations. All conditions were run in duplicate and each reaction was allowed to proceed for 3 hours at 60° C. and then was quenched by 3× dilution in NaSCN solution (specific for each such that final Pd:SCN⁻ was kept at 1:2). HPLC analyses were performed on samples diluted 5 fold into 8 M urea/20 mM TCEP, using method 3, Example 3. FIG. 2 illustrates the yield of rGRF(1-44) amide as a function of malonic acid, precursor peptide and tetrachloropalladate concentrations.

As can be seen in FIG. 2, by comparing the (4 M, 2 mg/mL) trend to the (4 M, 3 mg/mL) as well as the (5 M, 2 mg/mL) curve to the (5 M, 3 mg/mL), there is very little difference in maximum yield associated with peptide concentration. However, comparison of (4 M, 2 mg/mL) to (5 M, 2 mg/mL), and also (4 M, 3 mg/mL) to (5 M, 3 mg/mL), shows a definite advantage of 4 M malonic acid concentration regardless of precursor peptide concentration. All four curves in FIG. 2 demonstrate a maximum for the tetrachloropalladate concentration that corresponds to 5-5.5 equivalents of tetrachloropalladate per cysteine residue (3 Cys/precursor peptide)

EXAMPLE 6

Comparison of the Cleavage-amidation of T7tag-Vg-D4KCH-GRF(1-44)-CAMLE (SEQ ID NO:20), T7tag-Vg-D4KCH-GRF(1-44)-CACLE (SEQ ID NO:11), and T7tag-Vg-D4KCH-GRF(1-44)-CAHLE (SEQ ID NO:21) by Tetrachloropalladate in Malonic Acid The -CAMLE (SEQ ID NO:16), -CAHLE (SEQ ID NO:17), and -CACLE (SEQ ID NO:12) precursor peptides, prepared in solution in 5 M malonic acid as described in Examples 1 and 2, were incubated with 4 mM tetrachloropalladate at 60° C. for 2 hours. Analyses were performed by method 1. The CACLE (SEQ ID NO:12) precursor peptide cleavage and amidation yields were double those of the CAHLE (SEQ ID NO:17) precursor peptide (31 vs 16.1% yield of GRF(1-44)amide), and CAMLE (SEQ ID NO:16) precursor peptide cleavage and amidation was 17 fold less than that of the CACLE (SEQ ID NO:12) precursor peptide (1.8% vs 31% yield of GRF(1-44)amide). Use of the CACLE (SEQ ID NO:12) tail sequence was therefore shown to yield the greatest amount of C-terminally amidated GRF.

EXAMPLE 7

Comparison of the Cleavage-amidation of T7tag-Vg-D4KCH-GRF(1-44) -CGHLE (SEQ ID NO:22), T7tag-Vg-D4KCH-GRF(1-44)-CAHLE (SEQ ID NO:21), T7tag-Vg-D4KCH-GRF(1-44)CLHLE (SEQ ID NO:23) by Tetrachloropalladate in Malonic Acid The precursor peptides T7tag-Vg-D4KCH-GRF(1-44)-CGHLE (SEQ ID NO:22), T7tag-Vg-D4KCH-GRF(1-44)-CAHLE (SEQ ID NO:21), T7tag-Vg-D4KCH-GRF(1-44)-CLHLE (SEQ ID NO:23) were solubilized in 5 M malonic acid as described in Examples 1 and 2, and were incubated with 4 mM tetrachloropalladate at 60° C. for 2 hours. HPLC analyses were performed by HPLC Method 1 of Example 3. The resultant amidation yields of the -CLHLE (SEQ ID NO:33) and -CAHLE (SEQ ID NO:17) precursors were essentially identical; both yielded about 50% more amide than the -CGHLE (SEQ ID NO:34) precursor. The results of this set of experiments established that $X_2$ in the tail sequence $Cys-X_2-X_3$ is not limited to any particular amino acid.

EXAMPLE 8

Comparison of the Cleavage-amidation of T7tag-Vg-D4KCH-GRF(1-44)-CACLE (SEQ ID NO:11), T7tag-Vg-D4KCH-GRF(1-44)-CACKK (SEQ ID NO:19), and T7tag-Vg-D4KCH-GRF(1-44)-CACDD (SEQ ID NO 18), by Tetrachloropalladate in Malonic Acid The precursor peptides T7tag-Vg-D4KCH-GRF(1-44)-CACLE (SEQ ID NO:11), T7tag-Vg-D4KCH-GRF(1-44)-CACKK (SEQ ID NO:19), and T7tag-Vg-D4KCH-GRF(1-44)-CACDD (SEQ ID NO:18) were solubilized in 5 M malonic acid as described in Examples 1 and 2, and were incubated with 4 mM tetrachloropalladate at 60° C. for 2 hours. HPLC analyses were performed by method 1 of Example 3. About 21% of the precursor CACKK (SEQ ID NO:14) amidated; the amidation yield of the other constructs averaged around 50%.

EXAMPLE 9

Figure 3A:
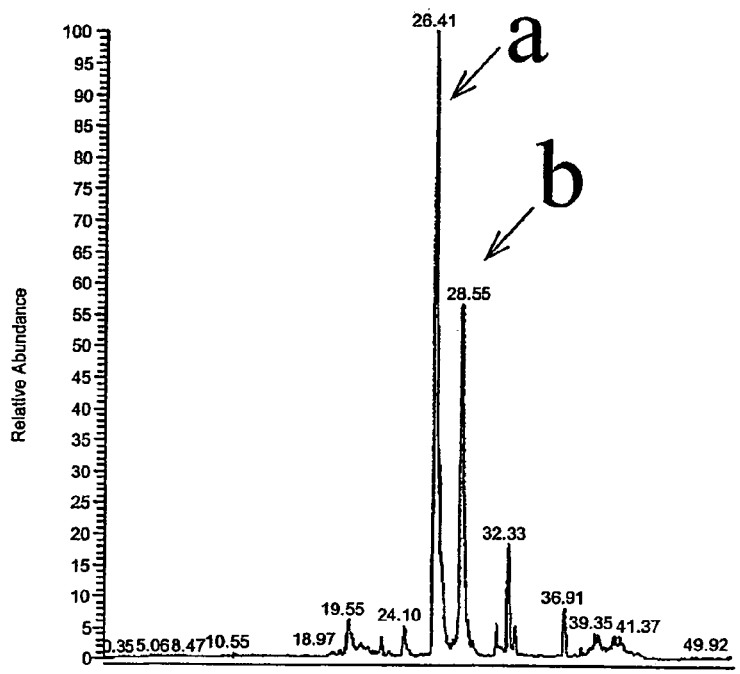
FIG. 3A is a total ion chromatogram.
Figure 3B:
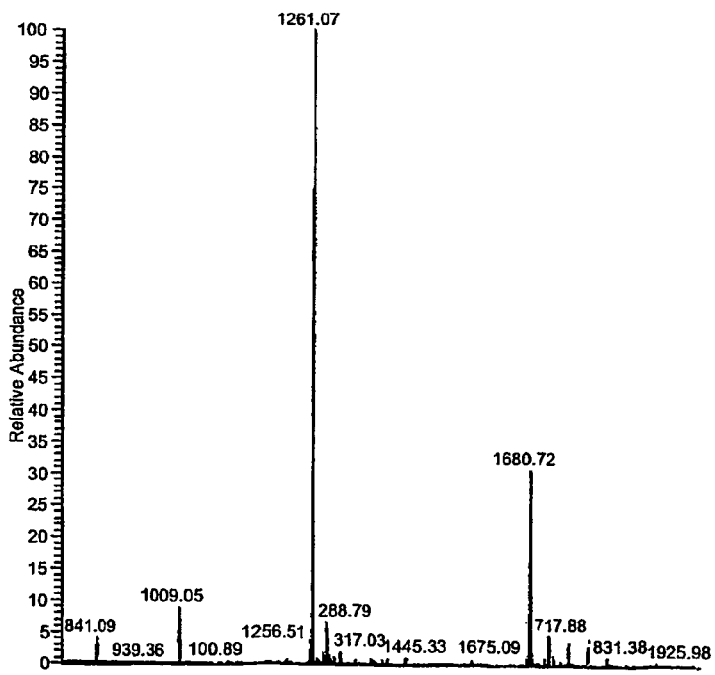
FIG. 3B is a mass spectroscopy analysis of peak a: rGRF(1-44)amide.
Figure 3C:
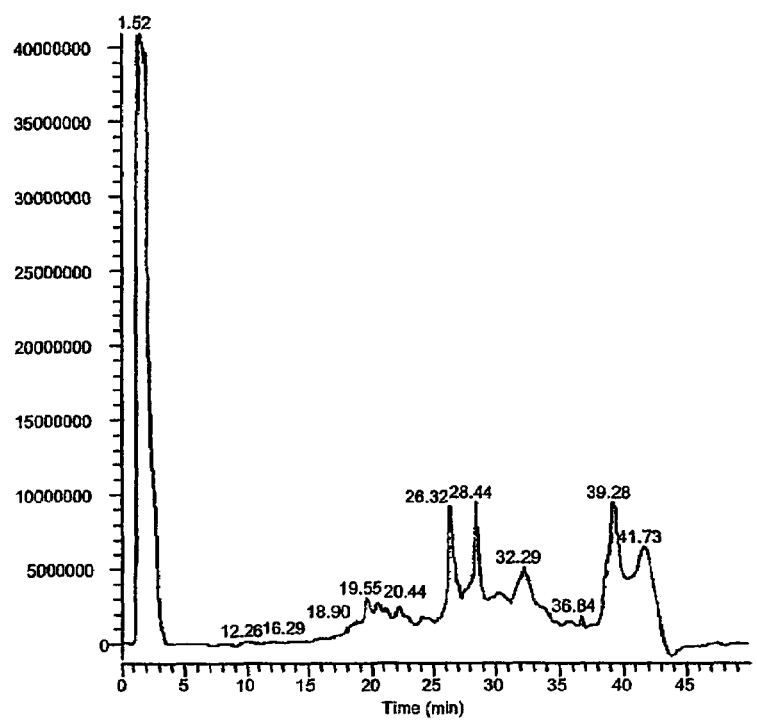
FIG. 3C is a ultraviolet chromatogram.
Figure 3D:
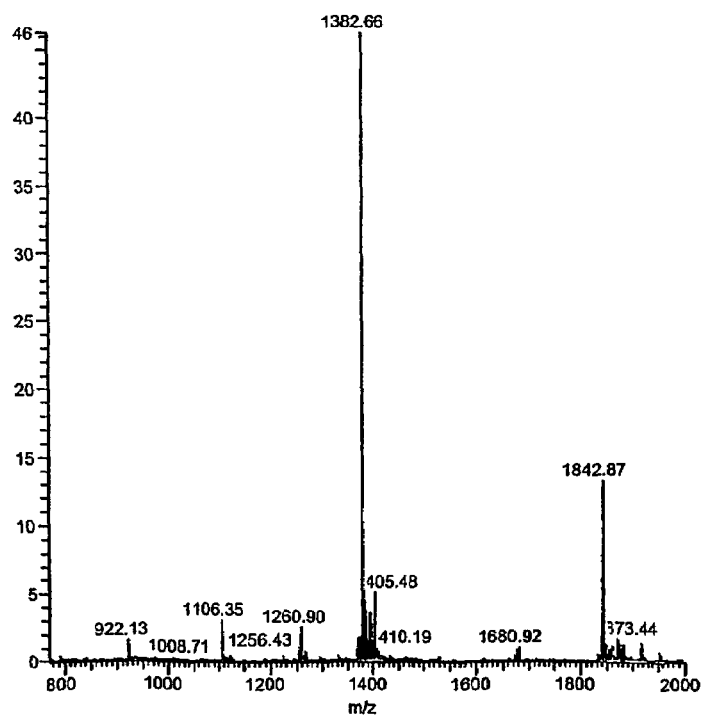
FIG. 3D is a mass spectroscopy analysis of peak b: rGRF(1-44)JACLE.

Mass Spectrometric Investigation of the Reaction Products of T7tag-Vg-D4KCH-GRF (1-44)-CACLE (SEQ ID NO:11) with Tetrachloropalladate in Malonic Acid The precursor peptide T7tag-Vg-D4KCH-GRF(1-44)-CACLE (SEQ ID NO:11) was solubilized in 5 M malonic acid at a concentration of 3 mg/mL, as described in Examples 1 and 2. The solution was incubated with 4 mM tetrachloropalladate at 60° C. for 2.5 hours. An aliquot of the solution was analyzed by LC-MS by HPLC method 2 of Example 3. FIG. 3A is rGRF(1-44)amide. FIG. 3C is rGRF(1-44)JACLE (SEQ ID NO:35).

The mass-spectrum of the putative GRF-product showed the correct mass for GRF(1-44)amide, as shown in FIG. 3. FIG. 3B is rGRF(1-44)amide. FIG. 3D is rGRF(1-44)JACLE (SEQ ID NO:35).

EXAMPLE 10

HPLC Identification of the Product of the Tetrachloropalladate Reaction with T7tag-Vg-D$_4$KCH-GRF (1-44)-CACLE (SEQ ID NO:11) in Malonic Acid as GRF(1-44)-amide T7tag-Vg-D4KCH-GRF(1-44)-CACLE (SEQ ID NO:11) precursor peptide was reacted with tetrachloropalladate as described in Example 9, and was analyzed by HPLC method 1 of Example 3. The cleavage-amidation product was analyzed with and without spiking standards of GRF(1-44)amide and GRF(1-44)-OH. The retention times for the standards were respectively 18.3 and 18.7 min. The product peak from the reaction eluted at 18.3 min. When the standards were added to the sample and then analyzed, the major peak at 18.3 min increased in height. This supports the mass-spectrometric identification of the product as being GRF(1-44)amide, and not GRF(1-44) free acid.

All publications, patents and patent applications including priority patent application No. 60/383,362 filed on May 24, 2002 are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A process to form a carboxyl-terminal amide of a desired peptide comprising contacting a substrate polypeptide and a palladium complex, where the palladium complex is a palladium(II) or palladium(IV) complex, in an acidic medium, wherein the substrate polypeptide comprises the sequence of the desired peptide and the sequence $X_1$-Cys-$X_2$-$X_3$; wherein $X_1$ is the amino acid at the carboxyl-terminus of the desired peptide, wherein $X_1$ and $X_2$ can be any amino acid, and wherein $X_3$ is selected from the group consisting of cysteine, histidine, and methionine.

2. The process of claim 1, wherein $X_2$ is alanine.

3. The process of claim 1, wherein the substrate polypeptide comprises two or more $X_1$-Cys-$X_2$-$X_3$ sequences.

4. The process of claim 3, wherein at least one of the $X_1$-Cys-$X_2$-$X_3$ sequences is positioned at the amino-terminus of the desired polypeptide and at least one of the $X_1$-Cys-$X_2$-$X_3$ sequences is positioned at the carboxyl-terminus of the desired peptide.

5. The process of claim 1, wherein the substrate polypeptide has a structure selected from the group consisting of (desired peptide-$X_1$)-(cysteine-$X_2$-$X_3$), (desired peptide-$X_1$)-(cysteine-$X_2$-$X_3$-tail sequence), (leader polypeptide-palladium cleavage site)-(desired peptide-$X_1$)-(cysteine-$X_2$-$X_3$-tail sequence), and (leader polypeptide-palladium cleavage site)-(desired peptide-$X_1$)-(cysteine-$X_2$-$X_3$); wherein $X_1$ is the amino acid at the carboxyl-terminus of the desired peptide, wherein $X_1$ and $X_2$ can be any amino acid, and wherein $X_3$ is selected from the group consisting of cysteine, histidine, and methionine.

6. The process of claim 5, wherein the tail sequence comprises an amino acid sequence selected from the group consisting of CACLE (SEQ ID NO:12), CACDD (SEQ ID NO:13), CACKK (SEQ ID NO:14), CKCLE (SEQ ID NO:15), CAMLE (SEQ ID NO:16), CAHLE (SEQ ID NO:17), CGHLE (SEQ ID NO:34), and CLHLE (SEQ ID NO:33).

7. The process of claim 5, wherein the (leader polypeptide-palladium cleavage site) comprises cysteine-histidine.

8. The process of claim 7, wherein the leader polypeptide is selected from the group consisting of DDDD (SEQ ID NO:36), DDDK (SEQ ID NO:37), DTRL (SEQ ID NO:38), and GGPR (SEQ ID NO:39).

9. The process of claim 7, wherein a leader sequence is present on the N-terminal side of the cysteine of the cleavage site.

10. The process of claim 9, wherein the leader sequence is DDDDK (SEQ ID NO:7) or GGGGPR (SEQ ID NO:8).

11. The process of claim 1, wherein prior to contacting the substrate polypeptide and the palladium complex, the substrate polypeptide is recombinantly expressed in a host cell as a chimeric protein and is recovered from the host cell in the form of an inclusion body.

12. The process of claim 11, wherein (a) the host cell is *E. Coli*; and (a) the chimeric protein is selected from the group consisting of $T_7$-Vg-$D_4$KCH-GRF (1-44)-CACLE (SEQ ID NO:11), $T_7$-Vg-$D_4$KCH-GRF (1-44)-CACDD (SEQ ID NO:18), $T_7$-Vg-$D_4$KCH-GRF (1-44)-CACKK (SEQ ID NO:19), $T_7$-Vg-$D_4$KCH-GRF (1-44)-CKCLE (SEQ ID NO:41), $T_7$Vg-$D_4$KCH-GRF (1-44)-CAMLE (SEQ ID NO:$_{20}$), $T_7$-Vg-$D_4$KCH-GRF (1-44)-CAHLE (SEQ ID NO:21), $T_7$-Vg-$D_4$KCH-GRF (1-44)-CGHLE (SEQ ID NO:22) and, $T_7$-Vg-$D_4$KCH-GRF (1-44)-CLHLE (SEQ ID NO:23).

13. The process of claim 1, wherein the substrate polypeptide is synthetic.

14. The process of claim 1, wherein the substrate polypeptide is naturally occurring.

15. The process of claim 1, wherein the substrate polypeptide is $T_7$-Vg-$D_4$KCH-GRF (1-44)-CACLE (SEQ ID NO:11), the acidic medium is malonic acid in a concentration of from about 4M to about 5M, the concentration of substrate polypeptide to malonic acid in the reaction mixture ranges from about 0.1 mg substrate polypeptide/ml malonic acid to about 3 mg substrate polypeptide/ml malonic acid, the palladium complex is $Na_2PdCl_4$ which is present in the reaction mixture in a molar concentration relative to cysteine in the substrate polypeptide of from about 4 to about 6, the reaction time is from about 60 to about 90 minutes, and the reaction temperature is about 60° C.

16. The process of claim 1, wherein prior to contacting the substrate polypeptide and the palladium complex the substrate polypeptide is expressed recombinantly in a host cell and is recovered from the host cell in the form of an inclusion body.

17. The process of claim 16, wherein the host cell is *E. coli*.

18. The process of claim 1, wherein the desired peptide is gastrin, calcitonin, luteinizinghormone-releasing hormone, pancreatic polypeptide, endothelin, corticotropin releasing factor, neuropeptide Y, atrial naturetic peptide, amylin, galanin, a somatostatin, vasoactive intestinal peptide or insulin.

19. The process of claim 18, wherein prior to contacting the substrate polypeptide and the palladium complex the substrate polypeptide is expressed recombinantly in a host cell and is recovered from the host cell in the form of an inclusion body.

20. The process of claim 1, wherein the desired peptide is GLP-2, GLP-1, GRF, PTH, parathyroid hormone related hormone, ACTH, an enkephalin, an endorphin, an exendin, an amylin, an opioid, gaegurin 5 or 6, brevinin 1, any one of ranatuerin 1 through 9, an esculetin, GIP, glucagon, motilin, a thymopoietin, a thymosin, ubiquitin, serum thymic factor, thymic humoral factor, neurotensin, or tuftsin.

21. The process of claim 20, wherein prior to contacting the substrate polypeptide and the palladium complex the substrate polypeptide is expressed recombinantly in a host cell and is recovered from the host cell in the form of an inclusion body.

22. The process of claim 21, wherein the host cell is *E. coli*.

23. The process of claim 1, wherein the acidic medium is an acidic organic solvent.

24. The process of claim 1 or 23, wherein the palladium complex is a Palladium(II) complex selected from the group consisting of $Na_2PdCl_4$; cis-[Pd(en)$Cl_2$]; cis-[Pd(bp)$Cl_2$]; cis-[Pd(phen)$Cl_2$]; cis-[Pd(pn)$Cl_2$]; cis-[Pd(pic)$Cl_2$]; cis-[Pd(dtco-OH)$Cl_2$ cis-[Pd(en)$(OH_2)_2]_{2+}$, cis-[Pd(pn)$(HO_2)_2]_{2+}$, cis-[Pd(pic)$(HO_2)_2]_{2+}$, cis-[Pd(bp)$(OH_2)_2]_{2+}$, cis-[Pd(phen)$(HO_2)_2]_{2+}$, cis-[Pd(dtco-OH)$(OH_2)_2]_{2+}$; and[Pd$(OH_2)_3$(OH)](NO$_3$).

25. The process of claim 23 wherein the acidic organic solvent is an monocarboxylic acid, dicarboxylic acid, tricarboxylic acid, hydroxysubstituted acid, uronic acid, aldonic acid or aldaric acid.

26. The process of claim 23, wherein the organic solvent is combined with an inorganic acid selected from the group consisting of HCl, $H_3PO_4$, $H_2SO_4$, and $HClO_4$.

27. The process of claim 23, wherein the molar ratio of palladium complex to Cys is from about 0.1 to about 20.

28. The process of claim 27, wherein the substrate polypeptide and palladium complex are contacted from about one to about two hours.

29. The process of claim 27, wherein the substrate polypeptide and palladium complex are contacted from about three to about six hours.

30. The process of claim 28, wherein the temperature is maintained at about 50° C. to about 70°C.

31. A process of producing a carboxyl-terminal amidated desired peptide comprising cleaving a substrate polypeptide concurrently at (i) a first cleavage site which links the N-terminus of a first amino acid sequence defining the desired peptide to the carboxyl terminus of a second amino acid sequence defining a leader sequence and (ii) at a second $X_1$-cysteine cleavage site, wherein $X_1$ is the amino acid at the peptide carboxy-terminus and the cysteine is the first amino acid of a tail sequence comprising the sequence cysteine -$X_2$-$X_3$, where $X_2$ is any amino acid and $X_3$ is an amino acid selected from the group consisting of cysteine, histidine, and methionine, by reacting the substrate polypeptide in a reaction mixture of an acidic organic solvent and a palladium complex, where the palladium complex is a palladium(II) or palladium(IV) complex, wherein the concentration of the organic solvent is between about 2 to about 22 molar and the carboxy-terminus of the desired peptide is amidated upon cleavage at the second $X_1$-cysteine cleavage site.

* * * * *

UNITED STATES PATENT AND TRADEMARK OFFICE
Certificate

Patent No. 7,462,690 B2

Patented: December 9, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Barton Holmquist, Eagle, NE (US); Daniel Strydom, Lincoln, NE (US); and Jin Seog Seo, Mississauga (CA).

Signed and Sealed this Twenty-first Day of February 2012.

CECILIA J. TSANG
*Supervisory Patent Examiner*
Art Unit 1654
Technology Center 1600